US007601132B2

(12) United States Patent
Nichols et al.

(10) Patent No.: US 7,601,132 B2
(45) Date of Patent: Oct. 13, 2009

(54) METHOD AND APPARATUS FOR APPLYING TRACTION TO THE SPINAL COLUMN

(75) Inventors: Jarrod L. Nichols, Manhattan, KS (US); Galen R. Ackerman, Sabetha, KS (US)

(73) Assignee: Nichols Therapy Systems, LLC, Manhattan, KS (US)

( * ) Notice: Subject to any disclaimer, the term of this patent is extended or adjusted under 35 U.S.C. 154(b) by 175 days.

(21) Appl. No.: 11/464,303

(22) Filed: Aug. 14, 2006

(65) Prior Publication Data

US 2007/0043315 A1 Feb. 22, 2007

Related U.S. Application Data

(60) Provisional application No. 60/708,749, filed on Aug. 16, 2005.

(51) Int. Cl.
*A61F 5/00* (2006.01)
*A61H 1/00* (2006.01)

(52) U.S. Cl. .............................. 602/32; 602/1; 602/33; 602/34; 602/35; 602/36; 602/38; 601/25; 601/26; 601/1; 601/24

(58) Field of Classification Search .................. 602/32, 602/34–36, 38, 1, 33; 601/1, 23, 24, 25, 601/26
See application file for complete search history.

(56) References Cited

U.S. PATENT DOCUMENTS 2,773,499 A * 12/1956 Zur Nieden .................. 602/32
3,768,464 A * 10/1973 Greissing ..................... 602/32
3,835,847 A * 9/1974 Smith .......................... 602/36
3,960,145 A 6/1976 Scarbrough
4,144,880 A * 3/1979 Daniels ...................... 606/242
4,915,101 A 4/1990 Cuccia
4,951,654 A * 8/1990 Gambale et al. ............ 606/242
5,129,881 A * 7/1992 Pope ........................... 602/32
5,409,452 A * 4/1995 Aversano ..................... 602/32
5,569,175 A * 10/1996 Chitwood .................... 602/32
5,922,011 A 7/1999 Cuccia
6,007,568 A 12/1999 Harrell et al.
6,039,737 A 3/2000 Dyer (Continued)

FOREIGN PATENT DOCUMENTS

RU 2181995 * 10/2002

OTHER PUBLICATIONS

Website page http://www.dynatronics.com/DX9.php regarding Dynatronics DX9 Decompression System (1 sheet).

(Continued)

*Primary Examiner*—Tarla R Patel
(74) *Attorney, Agent, or Firm*—Hovey Williams LLP

(57) ABSTRACT

A traction force is applied at an angle to the longitudinal axis of the patient's spine and progressively increased over a period of time. A fulcrum member is applied against the posterior portion of the cervical region of a person's spine while the traction force pulls the cervical region and bends it rearwardly about the fulcrum member to stretch the soft tissues of the spine. In preferred embodiments the fulcrum member applies a progressively increasing fulcrum force, and the traction force likewise progressively increases during the treatment period. An electronic control system may be used to automatically control application of the fulcrum and traction forces.

23 Claims, 16 Drawing Sheets

U.S. PATENT DOCUMENTS

| | | | | |
|---|---|---|---|---|
| 6,210,354 | B1 * | 4/2001 | Ousdal | 602/36 |
| 7,201,729 | B2 | 4/2007 | Emsky | |
| 2003/0114780 | A1 | 6/2003 | Al-Obaidi et al. | |
| 2006/0224097 | A1 * | 10/2006 | Bass | 602/32 |

OTHER PUBLICATIONS

Website page http://www.dynatronics.com/TX900.php regarding Dynatronics TX900 Traction Unit (1 sheet).

PCT Written Opinion of the International Searching Authority dated Aug. 9, 2007 (6 pgs/).

PCT Notification of Transmittal of the International Search Report and the Written Opinion of the International Search Authority, or the Declaration dated Aug. 9, 2007 (1 pg.).

PCT International Search Report dated Aug. 9, 2007 (3 pgs.).

* cited by examiner

| Today's Date: | Treatment Plan 1 | Birth Date | Sex | Activity Level | Height | Weight | BMI |
|---|---|---|---|---|---|---|---|
| *Start Date:* | | 1/0/1900 | 0 | Active | 69 | 185 | 27.3 |
| *Treatments per Week* 4 | | Patient: | Doe | | John A. | | 0 |

| Treatment Schedule | | | Mechanical Settings | | | Treatment Limits | | | Phase 1 | | Phase 2 | | Phase 3 | | Phase 4 | | Phase 5 | |
|---|---|---|---|---|---|---|---|---|---|---|---|---|---|---|---|---|---|---|
| Treatment Number | Treatment Date | Provider | Height | Fulcrum | Traction | Treatment Time | Peak Fulcrum | Peak Traction | % of Time | % of Peak | % of Time | % of Peak | % of Time | % of Peak | % of Time | % of Peak | % of Time | % of Peak |
| 1 | 9/8/2005 | Fred Smith D.C | 42 | 10 | B | 5 | 15.0 | 18.0 | 10 | 70 | 20 | 90 | 30 | 95 | 30 | 100 | 10 | 0 |
| 2 | 9/10/2005 | Fred Smith D.C | 42 | 10 | B | 6 | 16.0 | 19.0 | 10 | 70 | 20 | 90 | 30 | 95 | 30 | 100 | 10 | 0 |
| 3 | 9/12/2005 | Fred Smith D.C | 42 | 10 | B | 7 | 17.0 | 20.0 | 10 | 70 | 20 | 90 | 30 | 95 | 30 | 100 | 10 | 0 |
| 4 | 9/14/2005 | Fred Smith D.C | 42 | 10 | B | 8 | 18.0 | 21.0 | 10 | 70 | 20 | 90 | 30 | 95 | 30 | 100 | 10 | 0 |
| 5 | 9/16/2005 | Fred Smith D.C | 42 | 10 | B | 9 | 19.0 | 22.0 | 10 | 70 | 20 | 90 | 30 | 95 | 30 | 100 | 10 | 0 |
| 6 | 9/18/2005 | Fred Smith D.C | 42 | 10 | B | 10 | 20.0 | 23.0 | 10 | 70 | 20 | 90 | 30 | 95 | 30 | 100 | 10 | 0 |
| 7 | 9/20/2005 | Fred Smith D.C | 42 | 10 | B | 11 | 21.0 | 24.0 | 10 | 70 | 20 | 90 | 30 | 95 | 30 | 100 | 10 | 0 |
| 8 | 9/22/2005 | Fred Smith D.C | 42 | 10 | B | 12 | 22.0 | 25.0 | 10 | 70 | 20 | 90 | 30 | 95 | 30 | 100 | 10 | 0 |
| 9 | 9/24/2005 | Fred Smith D.C | 42 | 10 | B | 13 | 23.0 | 26.0 | 10 | 70 | 20 | 90 | 30 | 95 | 30 | 100 | 10 | 0 |
| 10 | 9/26/2005 | Fred Smith D.C | 42 | 10 | B | 14 | 24.0 | 27.0 | 10 | 70 | 20 | 90 | 30 | 95 | 30 | 100 | 10 | 0 |
| 11 | | | 42 | 10 | B | 15 | 25.0 | 28.0 | 10 | 70 | 20 | 90 | 30 | 95 | 30 | 100 | 10 | 0 |
| 12 | | | 42 | 10 | B | 16 | 26.0 | 29.0 | 10 | 70 | 20 | 90 | 30 | 95 | 30 | 100 | 10 | 0 |
| 13 | | | 42 | 10 | B | 17 | 27.0 | 30.0 | 10 | 70 | 20 | 90 | 30 | 95 | 30 | 100 | 10 | 0 |
| 14 | | | 42 | 10 | B | 18 | 28.0 | 31.0 | 10 | 70 | 20 | 90 | 30 | 95 | 30 | 100 | 10 | 0 |
| 15 | | | 42 | 10 | B | 19 | 29.0 | 32.0 | 10 | 70 | 20 | 90 | 30 | 95 | 30 | 100 | 10 | 0 |
| 16 | | | 42 | 10 | B | 20 | 30.0 | 33.0 | 10 | 70 | 20 | 90 | 30 | 95 | 30 | 100 | 10 | 0 |
| 17 | | | 42 | 10 | B | 20 | 31.0 | 34.0 | 10 | 70 | 20 | 90 | 30 | 95 | 30 | 100 | 10 | 0 |
| 18 | | | 42 | 10 | B | 20 | 32.0 | 35.0 | 10 | 70 | 20 | 90 | 30 | 95 | 30 | 100 | 10 | 0 |
| 19 | | | 42 | 10 | B | 20 | 33.0 | 36.0 | 10 | 70 | 20 | 90 | 30 | 95 | 30 | 100 | 10 | 0 |
| 20 | | | 42 | 10 | B | 20 | 34.0 | 37.0 | 10 | 70 | 20 | 90 | 30 | 95 | 30 | 100 | 10 | 0 |
| 21 | | | 42 | 10 | B | 20 | 35.0 | 38.0 | 10 | 70 | 20 | 90 | 30 | 95 | 30 | 100 | 10 | 0 |
| 22 | | | 42 | 10 | B | 20 | 36.0 | 39.0 | 10 | 70 | 20 | 90 | 30 | 95 | 30 | 100 | 10 | 0 |
| 23 | | | 42 | 10 | B | 20 | 37.0 | 40.0 | 10 | 70 | 20 | 90 | 30 | 95 | 30 | 100 | 10 | 0 |
| 24 | | | 42 | 10 | B | 20 | 38.0 | 41.0 | 10 | 70 | 20 | 90 | 30 | 95 | 30 | 100 | 10 | 0 |
| 25 | | | 42 | 10 | B | 20 | 39.0 | 42.0 | 10 | 70 | 20 | 90 | 30 | 95 | 30 | 100 | 10 | 0 |
| 26 | | | 42 | 10 | B | 20 | 40.0 | 43.0 | 10 | 70 | 20 | 90 | 30 | 95 | 30 | 100 | 10 | 0 |
| 27 | | | 42 | 10 | B | 20 | 40.0 | 43.0 | 10 | 70 | 20 | 90 | 30 | 95 | 30 | 100 | 10 | 0 |
| 28 | | | 42 | 10 | B | 20 | 40.0 | 43.0 | 10 | 70 | 20 | 90 | 30 | 95 | 30 | 100 | 10 | 0 |
| 29 | | | 42 | 10 | B | 20 | 40.0 | 43.0 | 10 | 70 | 20 | 90 | 30 | 95 | 30 | 100 | 10 | 0 |
| 30 | | | 42 | 10 | B | 20 | 40.0 | 43.0 | 10 | 70 | 20 | 90 | 30 | 95 | 30 | 100 | 10 | 0 |
| 31 | | | 42 | 10 | B | 20 | 40.0 | 43.0 | 10 | 70 | 20 | 90 | 30 | 95 | 30 | 100 | 10 | 0 |
| 32 | | | 42 | 10 | B | 20 | 40.0 | 43.0 | 10 | 70 | 20 | 90 | 30 | 95 | 30 | 100 | 10 | 0 |
| 33 | | | 42 | 10 | B | 20 | 40.0 | 43.0 | 10 | 70 | 20 | 90 | 30 | 95 | 30 | 100 | 10 | 0 |
| 34 | | | 42 | 10 | B | 20 | 40.0 | 43.0 | 10 | 70 | 20 | 90 | 30 | 95 | 30 | 100 | 10 | 0 |
| 35 | | | 42 | 10 | B | 20 | 40.0 | 43.0 | 10 | 70 | 20 | 90 | 30 | 95 | 30 | 100 | 10 | 0 |
| 36 | | | 42 | 10 | B | 20 | 40.0 | 43.0 | 10 | 70 | 20 | 90 | 30 | 95 | 30 | 100 | 10 | 0 |

*Fig. 13.*

METHOD AND APPARATUS FOR APPLYING TRACTION TO THE SPINAL COLUMN

RELATED APPLICATION

This application claims the priority benefit of provisional application Ser. No. 60/708,749 filed Aug. 16, 2005, which application is hereby incorporated by reference into the present specification.

BACKGROUND AND TECHNICAL FIELD

Traditionally, chiropractic has focused largely on a functional model of treatment and relies on the concept that manipulation of the spine allows improved functional movement, which in turn allows greater overall spinal function and general health. While this method has been shown to offer symptomatic relief to patients, manipulation in and of itself has not been shown to effectively or permanently improve or correct abnormal spinal structure.

Soft tissues associated with the spine and other body structures exhibit a unique characteristic known as "viscoelasticity." This property allows the soft tissue to return to its original shape and length if a submaximal force is applied for a relatively short period of time, such as, for example, less than five minutes. This explains why traditional spinal manipulation, with a typical duration of a fraction of a second, typically does not cause a permanent change in the structure of the spine.

On the other hand, soft tissues also exhibit the property of "plastic deformation", by which the tissues deform permanently if a force is applied thereto over a prolonged period of time. Thus, "extension" traction therapy, which applies a force at an angle to the longitudinal axis of the spine and typically for a duration of between five and twenty minutes, has been shown to consistently correct abnormal spinal curves.

The present invention relates to the field of extension traction therapy for correcting abnormal spinal curves and, in particular, to improved methods and equipment for use in that field. It has particular, but not exclusive, utility in correcting the shape of the cervical region of a person's spine. In doing so, it has related positive effect on the rest of the spine as well.

BRIEF DESCRIPTION OF THE DRAWINGS

FIG. 13 depicts a computer monitor screen displaying details of a patient's overall treatment plan including a series of individual treatments;

DETAILED DESCRIPTION OF A PREFERRED EMBODIMENT

The present invention is susceptible of embodiment in many different forms. While the drawings illustrate and the specification describes certain preferred embodiments of the invention, it is to be understood that such disclosure is by way of example only. There is no intent to limit the principles of the present invention to the particular disclosed embodiments.

Figure 6:
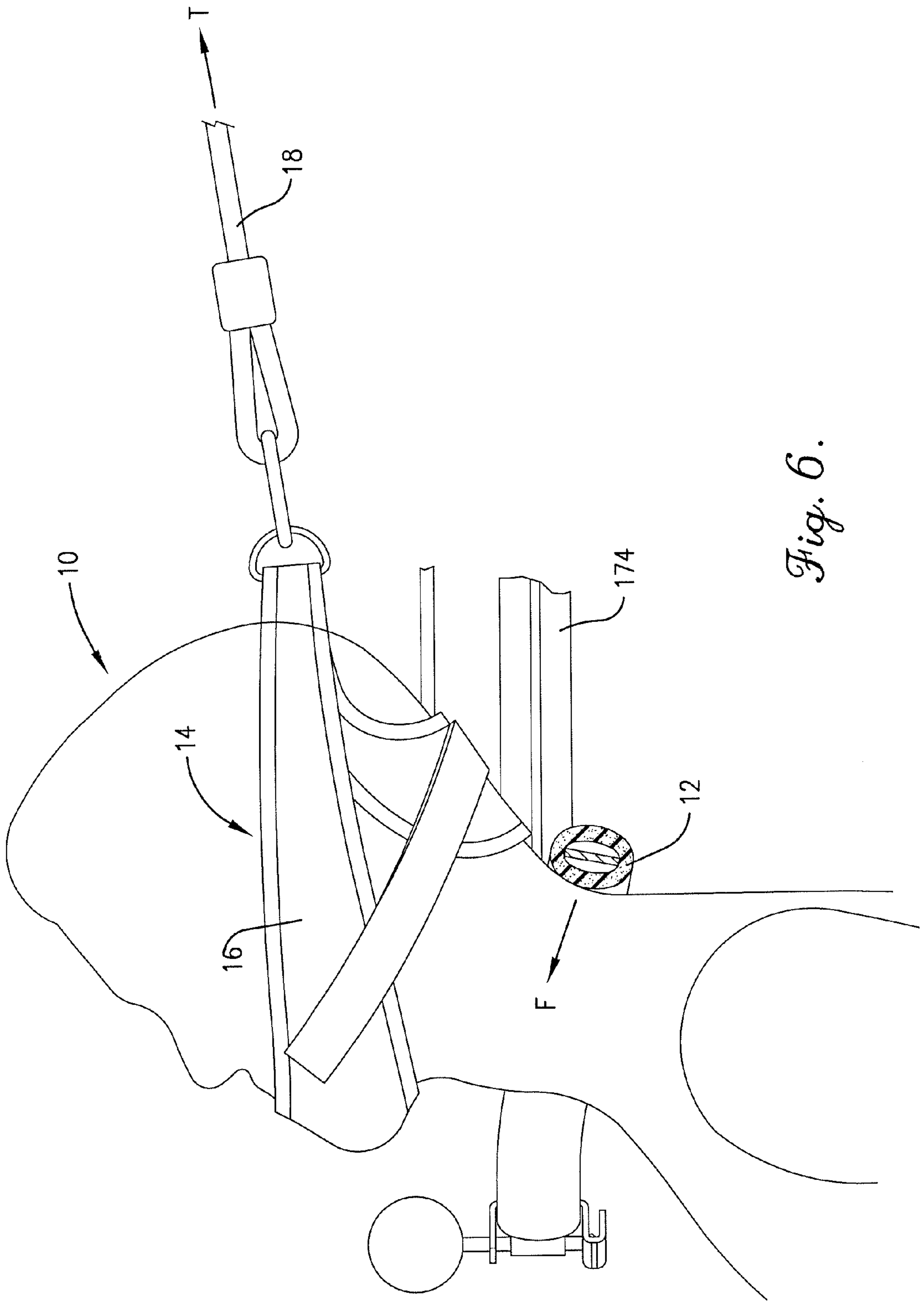
FIG. 6 is an enlarged, fragmentary left side elevational view similar to FIG. 5 but with parts broken away and shown in cross section to illustrate the manner in which the fulcrum assembly and traction assembly cooperate to exert restorative forces against the cervical region of the patient's spine during treatment.

The broad principles of the present invention as applied to the cervical region (neck) of a person 10 are illustrated in FIG. 6. As shown in that figure, in order to improve the biomechanical structure or shape of the spine, a pair of generally oppositely directed forces are applied to the cervical region. The first force is a forwardly directed fulcrum force F applied by a fulcrum member 12 against the posterior portion of the cervical region. The second force is an extension traction force T that pulls generally in the opposite direction at an angle to the longitudinal axis of the spine to bend the cervical region rearwardly about the fulcrum member 12 and stretch the soft tissues. In the illustrated embodiment, traction force T is applied through a headgear 14 that includes a chin strap 16 pulled upwardly and rearwardly by a cable or rope 18. As well understood by those skilled in the art, the illustrated headgear 14 is exemplary of any number of different means by which rope 18 could be operably coupled with the person's head. Likewise, while the illustrated embodiment shows the fulcrum member 12 as comprising a foam-covered strap, it will be appreciated that fulcrum member 12 may take a variety of different forms as well.

At least one of the forces F, T, and preferably both, are progressively increased for a predetermined period of time during the treatment period. While the increase may be "stair-stepped", in a most preferred arrangement, the progressive increase is substantially continuous. Such smooth, gradual increase over a significant period of time (such as more than five minutes, for example) can have the cumulative effect of stretching or plastically deforming the soft tissues associated with the cervical region to such an extent that the soft tissues are permanently reshapened after the forces are removed, while avoiding unacceptable discomfort for the patient.

In a most preferred embodiment, both the fulcrum force F and the traction force T will increase progressively and continuously at the same rate of progress, although perhaps in different amounts depending upon their respective peak forces, until their peaks are obtained. As one illustration of this preferred manner of operation, FIG. 14 comprises a graph of the percentage of peak force achieved during a treatment period against the percentage of elapsed treatment time. It will be noted in this illustration that after starting at zero percent, the continuously increasing force increases quickly at first and then slows down dramatically but continues to increase over the remaining portion of the treatment time until the peak percentage of 100% is reached. Upon reaching its peak value, the force quickly but progressively drops to zero, at which point the treatment is completed.

The treatment parameters, including for example peak force, rate of increase, and length of treatment time, will vary from patient-to-patient and from treatment-to-treatment. Different patients obviously have different needs, which means that the force and time values selected for different patients are likely to vary. Even with the same patient, it is contemplated that several different treatments will be involved over a period of several days or weeks, with each treatment typically being slightly different than the previous treatment.

FIG. 13 illustrates one form of treatment plan that might be used for a particular patient. In the plan of FIG. 13, column 20 identifies the treatment by number and indicates that for this particular patient ten out of thirty-six treatments have been completed. Column 22 "treatment time" sets forth the total length of treatment time that the doctor has selected for the particular patient. Thus, for treatment no. 1, a total of five minutes has been decided upon, while for treatment no. 10, a duration of fourteen minutes has been planned. During the five minutes of treatment time for the first treatment, the peak fulcrum force as reflected in column 24 is 15 lbs. Correspondingly, the peak traction force is 18 lbs., as reflected in column 26.

Figure 14:
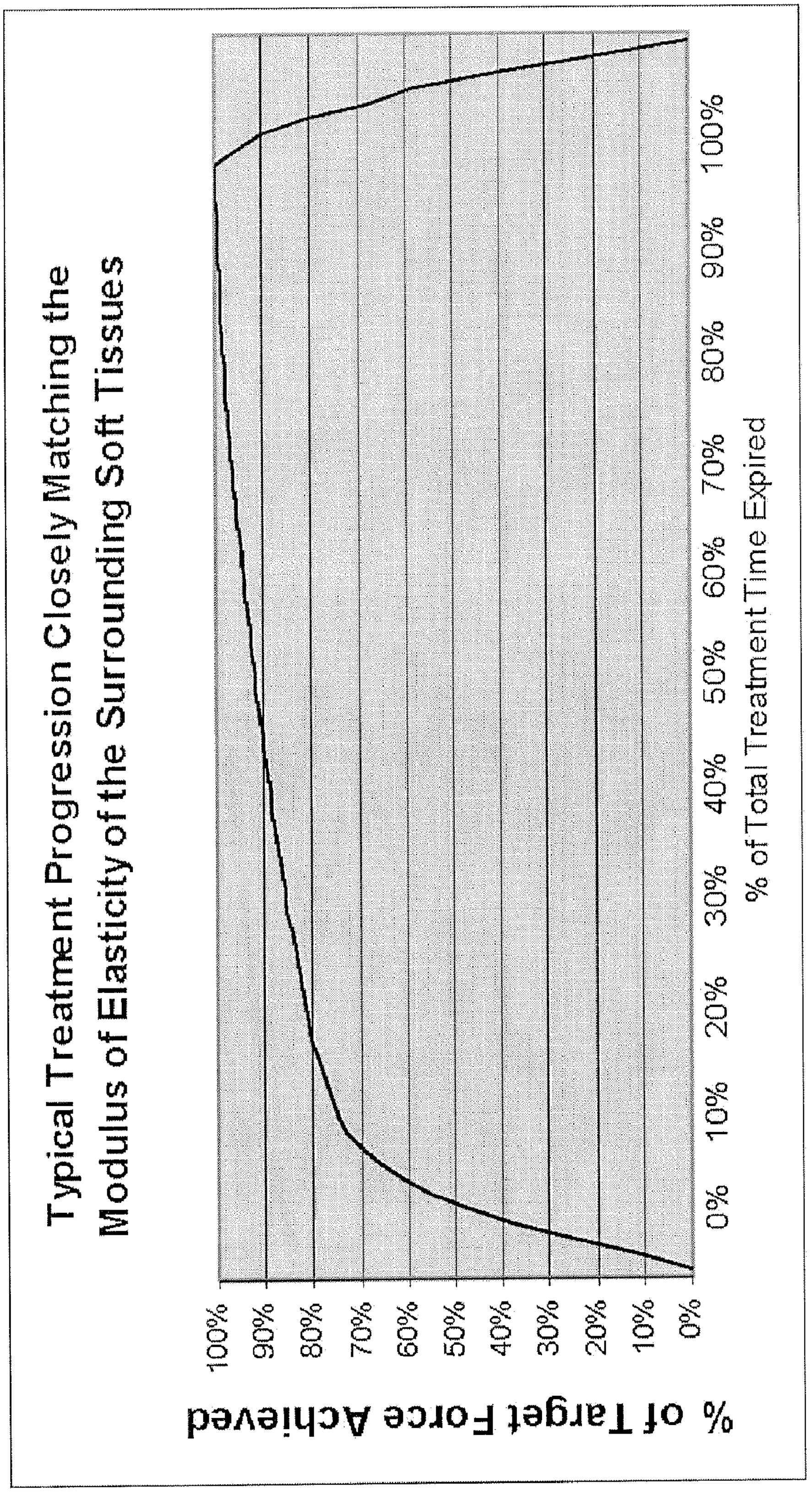
FIG. 14 is a graph of percentage of target force achieved versus percentage of total time elapsed for a typical treatment.

Preferably, the total treatment time maybe broken down into a number of time phases, for example five phases in total are reflected on the chart in FIG. 13. For each phase there is a column 28 for the "percentage of time" devoted to that phase out of the total treatment time, and also a column 30 "percentage of peak" which reflects the force level achieved at the end of that phase as a percentage of the peak force value for the entire treatment. Thus, in treatment no. 1, phase 1 lasts for 10% of the total treatment time, and by the end of that phase the force levels of the fulcrum force F and the traction force T are to have reached 70% of their peak values for the entire treatment period. This is reflected, for example, in the relatively sharp incline of the curve in FIG. 14 showing that the force values increase quickly in the early part of the treatment period.

Continuing with the example of treatment no. 1, by the end of phase 2, another 20% of the treatment time will have elapsed and the force value exerted will have reached 90% of its peak value. By the end of phase 3, another 30% of the treatment time will have elapsed and 95% of the peak value will be reached. By the end of phase 4 an additional 30% of the treatment time will have elapsed and the force value will have achieved 100% of its peak value. During phase 5, which accounts for 10% of the total treatment time, the force drops to zero by the end of that phase.

Figure 12:
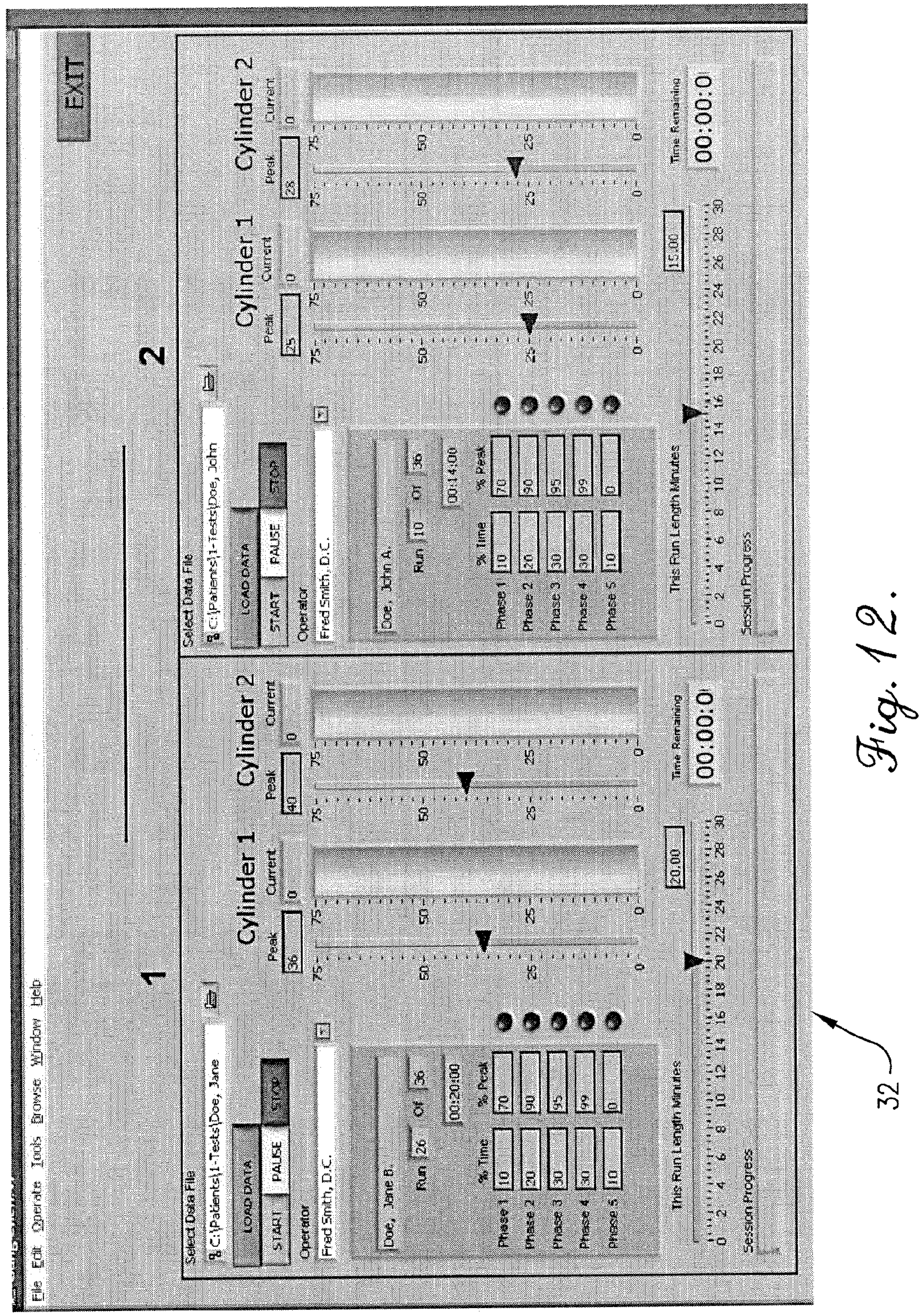
FIG. 12 depicts a computer monitor screen displaying details of current individual treatments and the status thereof for two different patients.

FIG. 12 is a screen shot taken from a computer monitor or the like displaying a screen for monitoring the ongoing treatment process, which process may be computer-controlled as hereinafter explained in more detail. In the particular illustration of FIG. 12, the treatments for two different patients are shown, simply to illustrate the point that more than a single patient may be receiving treatment at any one time, yet all patients can be monitored simultaneously.

For example, in the left hand portion of the screen 32 in FIG. 12 the status of the treatment for a first patient is displayed. The right hand portion of screen 32 displays information regarding the status of a second patient undergoing treatment. The term "cylinder 1" in each instance refers to the fulcrum force F while the term "cylinder 2" refers to the traction force T. A peak fulcrum force of 36 lbs. is indicated for the particular treatment in the left part of the screen, which is the 26th treatment of 36 total treatments, while the peak traction force for this particular treatment is 40 lbs. The run length or total treatment time for this treatment is indicated as 20 minutes, and it is divided into 5 phases with phase 1 consuming 10% of the total time, phase 2 consuming 20%, phase 3 consuming 30%, phase 4 consuming 30%, and phase 5 consuming 10%. By the end of phase 1, the force levels will have reached 70% of their peak, by the end of phase 2 they will have reached 90%, by the end of phase 3 they will have reached 95%, by the end of phase 4 they will have reached 100%, and by the end of phase 5 they will have dropped to 0%.

Referring now to the other Figures, one embodiment of a machine 40 for carrying out the progressive traction concepts of the present invention is disclosed. Machine 40 as illustrated is operable to produce both a progressively increasing fulcrum force and a progressively increasing traction force, although it is within the concepts of the present invention to have only one of such forces increasing while the other remains constant. For example, the fulcrum member 12 could simply comprise a stationary fulcrum member without movement in any direction while the traction force T increases over time. Conversely, the traction force T could remain constant and only the fulcrum force increased over time. In any event, as above noted, in the particular embodiment described in detail hereinafter, both the fulcrum force F and the traction force T are progressively increased over at least a predetermined portion of the total treatment period. In a most preferred form, the progressive increase is substantially continuous.

Machine 40 includes a frame broadly identified by the numeral 42 that supports all other portions of machine 40, with the exception of a personal computer or the like which may serve as part of the control system for machine 40 as hereinafter described. Frame 42 includes a generally I-shaped base 44 having a fore-and-aft extending longitudinal member 46 and a pair of transversely extending cross members 48, 50 at opposite ends thereof. Ground wheels 52 and 54 at opposite ends of rear cross member 48 adapt the machine 40 to be tipped up and rolled between different locations. Normally, wheels 52, 54 are spaced slightly above the floor or in only light engagement therewith while members 44, 48 and 50 provide the primary load-bearing engagement of the machine with the floor. A pair of non-skid pads 56 and 58 at opposite ends of the front cross member 50 normally engage the floor to help retain the machine in a selected position of use.

Frame 42 further includes an upright mast 60 having a lower, outer section 62 of rectangular cross sectional configuration and an upper, inner section 64 telescopically received within lower section 62. Lower section 62 is affixed at its lower end to longitudinal base member 46, whereas telescoping upper section 64 is fixed at its upper end to a cross head 66. Thus, cross head 66 is movable up and down as upper section 64 telescopes within lower section 62.

Cross head 66 is adjustably raised and lowered by a manually operable jack assembly 68. While jack assembly 68 may take a variety of different forms, one suitable such jack is available from Fulton Performance Products, Inc. of Mosinee, Wis. Jack assembly 68 includes a lower, internal, upright tube 70 and an upper, outer upright tube 72 telescopically received on lower tube 70. Outer tube 72 is fixed via connecting plates 74 and 76 to upper mast section 64 such that when outer tube 72 moves up and down, upper mast section 64 moves with it via the fixed connections provided by plates 74 and 76. A hand crank 78 rotatably supported on outer tube 72 of jack assembly 68 is operably coupled with internal mechanism (not shown) within jack assembly 68 causing telescoping movement of outer tube 72 when hand crank 78 is operated.

A pointer 80 at the lower front edge of connecting plate 76 moves along a vertical series of numbers 82 on a pair of mounting plates 84 that are fixed to and project forwardly from opposite sides of the stationary lower section 62 of mast 60. Numbers 82 provide the doctor with height values for establishing a repeatable selected height for cross head 66.

The mounting plates 84 on opposite sides of mast 60 project forwardly from outer section 62 and connect rigidly at their forward extremities to a generally L-shaped seat plate 86 having a generally upright leg 88 and a horizontal leg 90 projecting forwardly from the lower extremity of upright leg 88. Horizontal leg 90 is fixed along its bottom surface to the upper ends of a pair of upright struts 92 and 94 on cross member 50 of base 44. A seat cushion 96 is secured to horizontal leg 90, while a back rest cushion 98 is secured to upright leg 88. A pair of arm rests 100 and 102 are disposed on opposite sides of seat 96 at an appropriate height above the latter.

Figure 5:
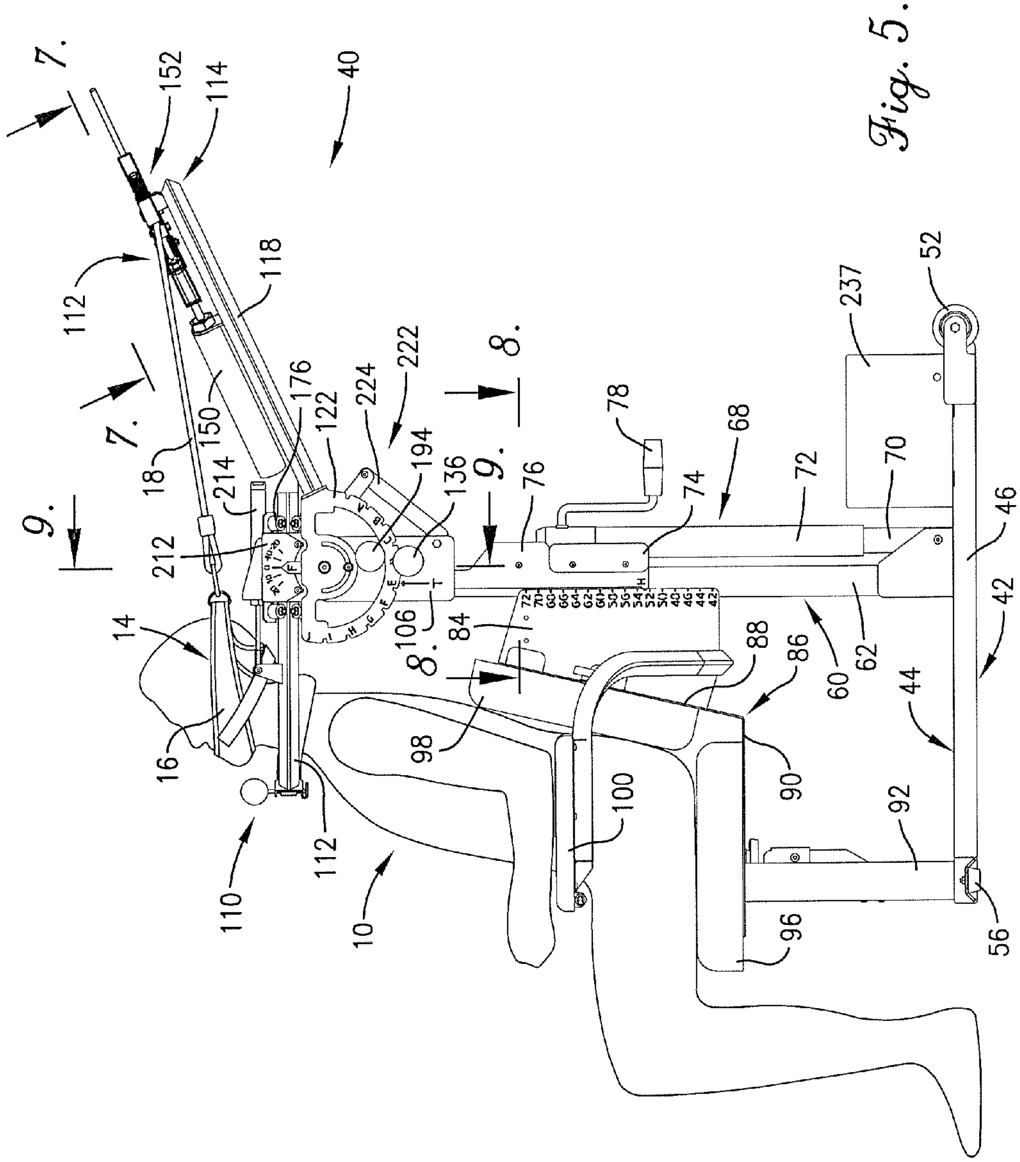
FIG. 5 is a left side elevational view of the machine and patient being treated.

It will thus be appreciated that the machine 40 is especially adapted to treat a person in a seated position and orientation as illustrated in FIG. 5. However, it will be understood that the principles of the present invention are not limited to having the patient seated. Indeed, in some instances it may be preferable to have the patient lying down, reclined, or standing.

Cross head 66 includes a transversely extending tubular frame member 104 of rectangular transverse cross sectional configuration. In addition, cross head 66 includes a pair of upright end plates 106 and 108 fixed to opposite ends of frame member 104 and projecting upwardly therefrom. The cross head 66, particularly the end plates 106, 108 supports a fulcrum assembly 110 and a traction assembly 112.

Dealing first with traction assembly 112, such assembly includes a rearwardly extending generally U-shaped yoke 114 having a rearwardly disposed bight 116 and a pair of legs 118 and 120 integral with bight 116 and extending forwardly from opposite lateral ends thereof. At their forwardmost ends, legs 118, 120 are rigidly fixed to respective crescents 122 and 124 that are secured by respective pivots 126 and 128 to the end plates 106, 108 near the upper ends thereof. Yoke 114 is thus rendered swingably adjustable up and down about a transverse axis defined by the aligned pivots 126, 128.

A releasable latch 130 is provided for releasably retaining yoke 114 in a selected angular position about pivots 126, 128. While latch 130 may take a variety of different forms, such as a simple set screw or the like to provide infinite adjustment, in the illustrated embodiment latch 130 comprises a long lock bar 132 that spans the two end plates 106, 108 and passes through corresponding slots 134 therein to project outwardly beyond respective plates 106, 108. Knobs 136 are attached to opposite ends of lock bar 132 to facilitate manual gripping and operation thereof. Adjacent each end of bar 132, a pair of notches 138 and 140 are provided along its upper edge, the notches 138, 140 being separated by a tab 142. Because lock bar 132 is shiftable lengthwise between end plates 106, 108, tabs 142 maybe positioned for locking engagement within any one of a series of downwardly projecting notches 144 in the corresponding crescents 122 and 124. By shifting lock bar 132 lengthwise either to the right or left of the machine, a corresponding pair of the notches 138 or 140 on bar 132 is brought into alignment with the lower edges of crescents 122, 124 to thereby unlatch the crescents and allow yoke 114 to be angularly adjusted about pivots 126, 128. By virtue of the two notches 138, 140 at each end of lock bar 132, latch 130 may be released by either a pushing or pulling action on lock bar 132 at either end thereof.

Lock bar 132 is yieldably retained in a position for latching engagement with crescents 122, 124. This is accomplished through the provision of a pair of compression springs 146 adjacent opposite ends of lock bar 132. Each spring 146 is captured within a corresponding aperture 148 in bar 132 and has an inner end **146*a* disposed for abutting engagement with the outside surface of the corresponding end plate 106 or 108. The left spring 146 exerts force in the opposite direction of the right spring 146 and in the same amount, such that the two springs 146 are operable to keep lock bar 132 yieldably disposed in a centered position wherein tabs 142 are aligned with corresponding crescents 122 and 124. Springs 146 thus operate to return lock bar 132 to a locked position following termination of the pushing or pulling force on lock bar 132 to unlatch the same. For convenience, the series of notches 144 along the arcuate lower extremity of each crescent 122 or 124 may be labeled with alphabet letters or other indicia to provide a visually observable indication of the selected angular position for yoke 114**.

Yoke 114 supports a fluid-pressure-operated power device 150 that is operably coupled with rope 18 for exerting the traction force T during the treatment period. In a most preferred embodiment, power device 150 is pneumatically operated and is thus coupled with a source of gas pressure via a control system as hereinafter more fully described.

Figure 7:
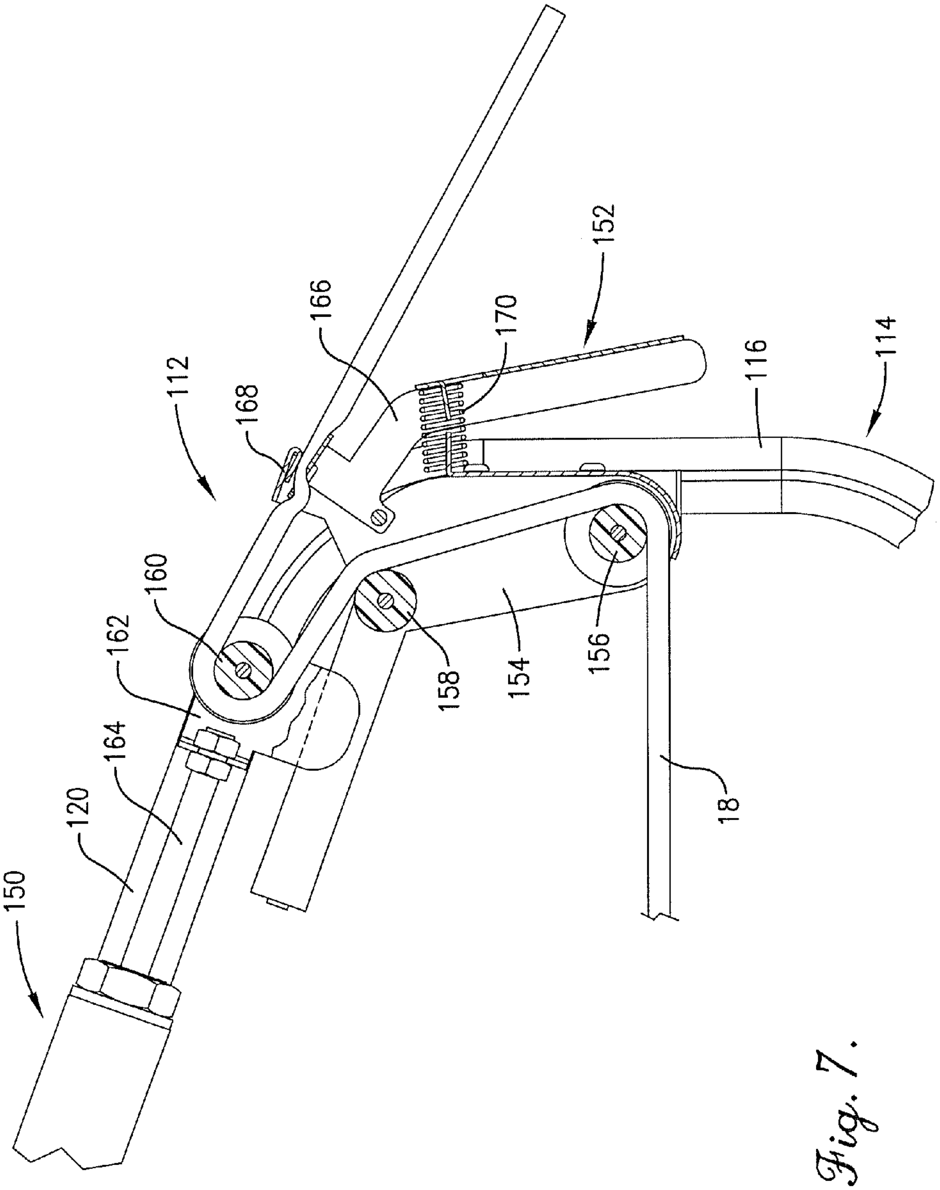
FIG. 7 is an enlarged, fragmentary top plan view of the traction assembly taken substantially along sight line 7-7 of FIG. 5 with parts broken away and shown in cross section to reveal details of construction.
Figure 8:
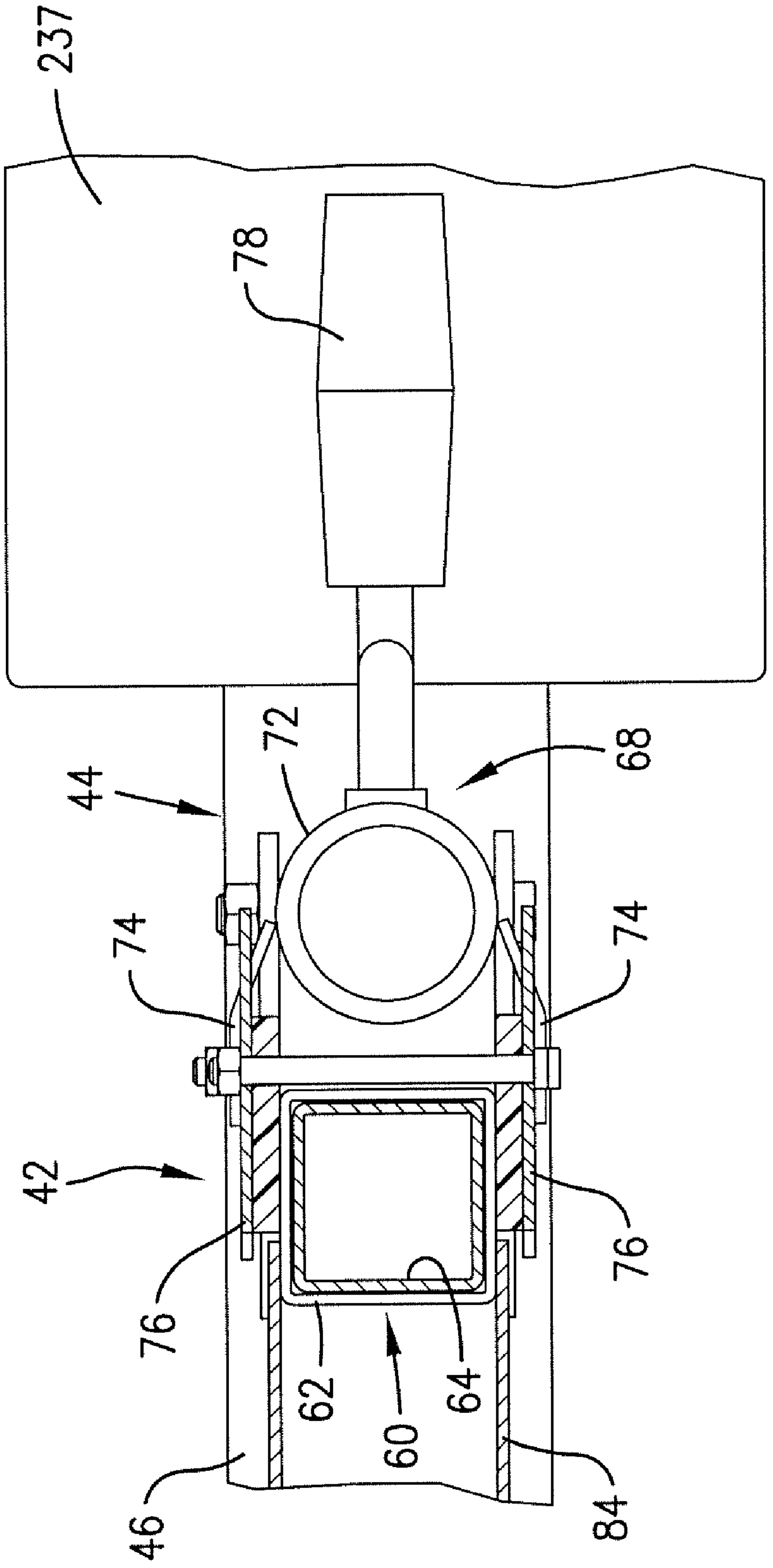
FIG. 8 is a fragmentary horizontal cross sectional view through the upright mast and adjacent structure of the machine taken substantially along line 8-8 of FIG. 5.

The mechanism by which rope 18 is coupled with traction cylinder 150 is illustrated in detail in FIG. 7 and is denoted broadly by the numeral 152. Such mechanism may take a variety of different forms. In the embodiment illustrated in FIG. 7, coupling mechanism 152 includes a bracket 154 that is fixedly attached to bight 116 of yoke 114. Bracket 154 carries a pair of idler rollers 156 and 158 that are entrained by rope 18 before the latter is back-wrapped around a third idler roller 160 on a lug 162 fixed to the proximal end of the rod 164 of air cylinder 150. From idler 160, the free end of rope 18 passes between the end of a spring-loaded clamp lever 166 and an opposed anvil 168 after passing through an opening in clamp lever 166. A compression spring 170 between bracket 154 and clamp lever 166 yieldably biases the latter toward a position tightly clamping the free end of rope 18 between clamp lever 166 and anvil 168. Thus, when rod 164 of air cylinder 150 retracts, idler 160 tends to pull additional length of the rope 118 from the section between idler 160 and head gear 14, rather than from the length between 160 and anvil 168. On the other hand, by squeezing clamp lever 166 toward bight 116 against the action of compression spring 170, the grip between anvil 168 and clamp lever 166 can be loosened sufficiently as to permit the length of rope 18 to be adjusted as may be necessary or desirable to accommodate different patients and different angles of adjustment for the traction assembly 112. It will be understood, of course, that as the rod 164 of air cylinder 150 retracts, the traction force T exerted by rope 18 is increased during the treatment of a patient.

The fulcrum assembly 110 includes, in addition to fulcrum member 12, a pair of fore-and-aft extending, bent arms 172 and 174 positioned at opposite ends of cross head 66. The front end of each arm 172, 174 terminates forwardly of cross head 66 generally adjacent the patient's head and on opposite sides thereof. Opposite ends of fulcrum member 12 are secured to the respective forward ends of fulcrum arms 172 and 174.

Straight portions of arms 172, 174 are received within respective left and right roller guides 176 and 178 for fore-and-aft shifting movement. Roller guides 176, 178 are fixed to respective left and right, semi-circular mounting plates 180, 182 supported on the inside faces of corresponding end plates 106, 108 by the same pivots 126, 128 that pivotally support crescents 122, 124. Thus, roller guides 176, 178, along with arms 172, 174 and fulcrum member 12, can be rocked about the horizontal axis defined by pivots 126, 128. Such rocking movement for angular adjustment of fulcrum assembly 110 is independent of adjustment or non-adjustment of traction assembly 112.

A transverse, elongated tie bar 184 spans the distance between mounting plates 180, 182 and is rigidly affixed thereto at its opposite ends to help provide structural rigidity to the fulcrum assembly 110. Tie bar 184 is downwardly bowed at its mid-section so as to assure clearance with the patient's head during treatment.

A releasable latch 186 is provided for releasably holding fulcrum assembly 110 in a selected position of angular adjustment about pivots 126, 128. Like traction assembly latch 130, fulcrum assembly latch 186 may take a variety of different forms, including for example a set screw or the like to provide infinite adjustment. In the illustrated embodiment latch 186 is similar in design to traction assembly latch 130 and includes a transverse lock bar 188 that spans the two end plates 106, 108 and passes through slots 190 therein to project a short distance beyond end plates 106, 108. Lock bar 188 also passes through a clearance opening 192 (FIG. 4) in each mounting plate 180, 182.

Figure 4:
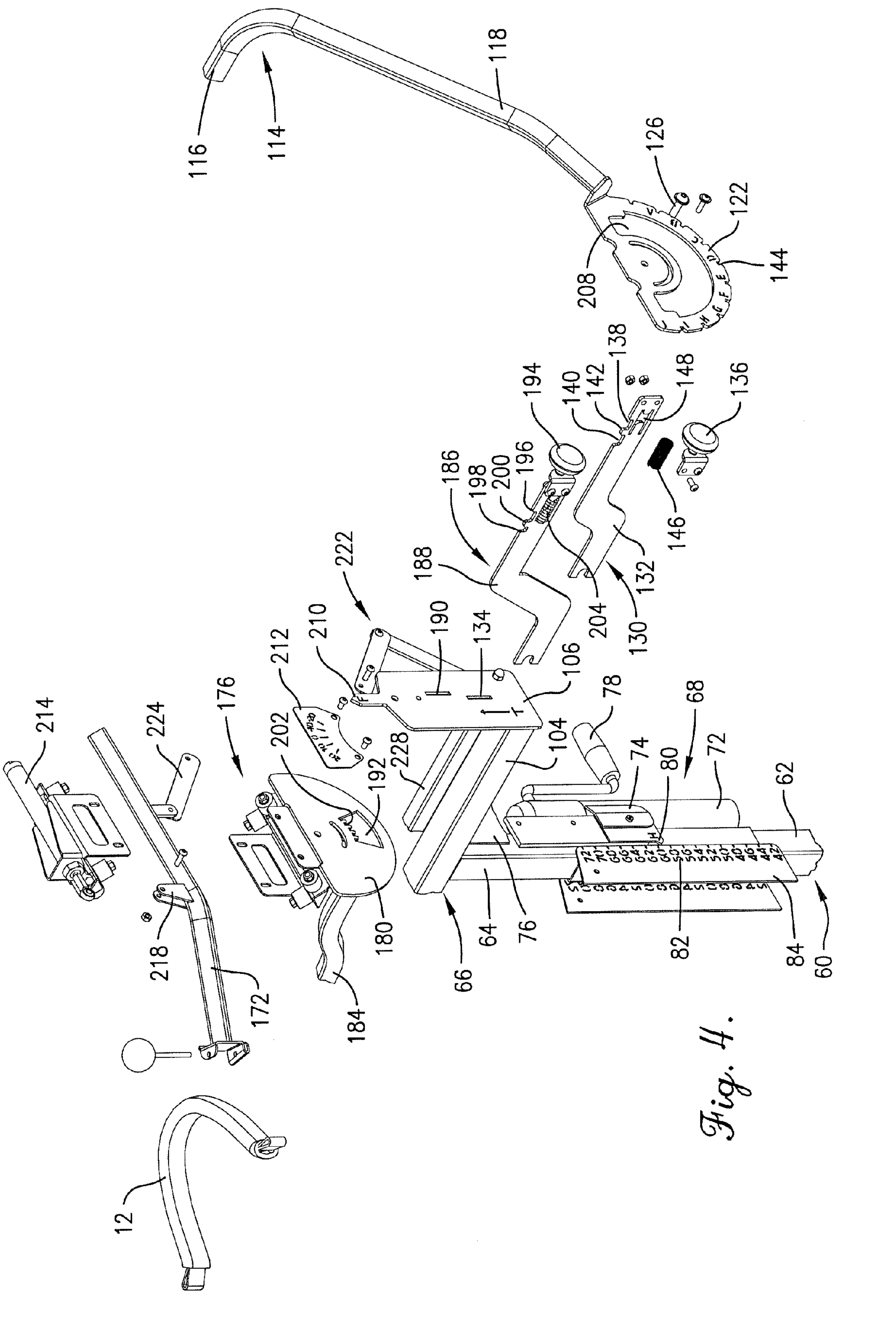
FIG. 4 is an exploded view of left upper portions of the machine illustrating details of construction.
Figure 9:
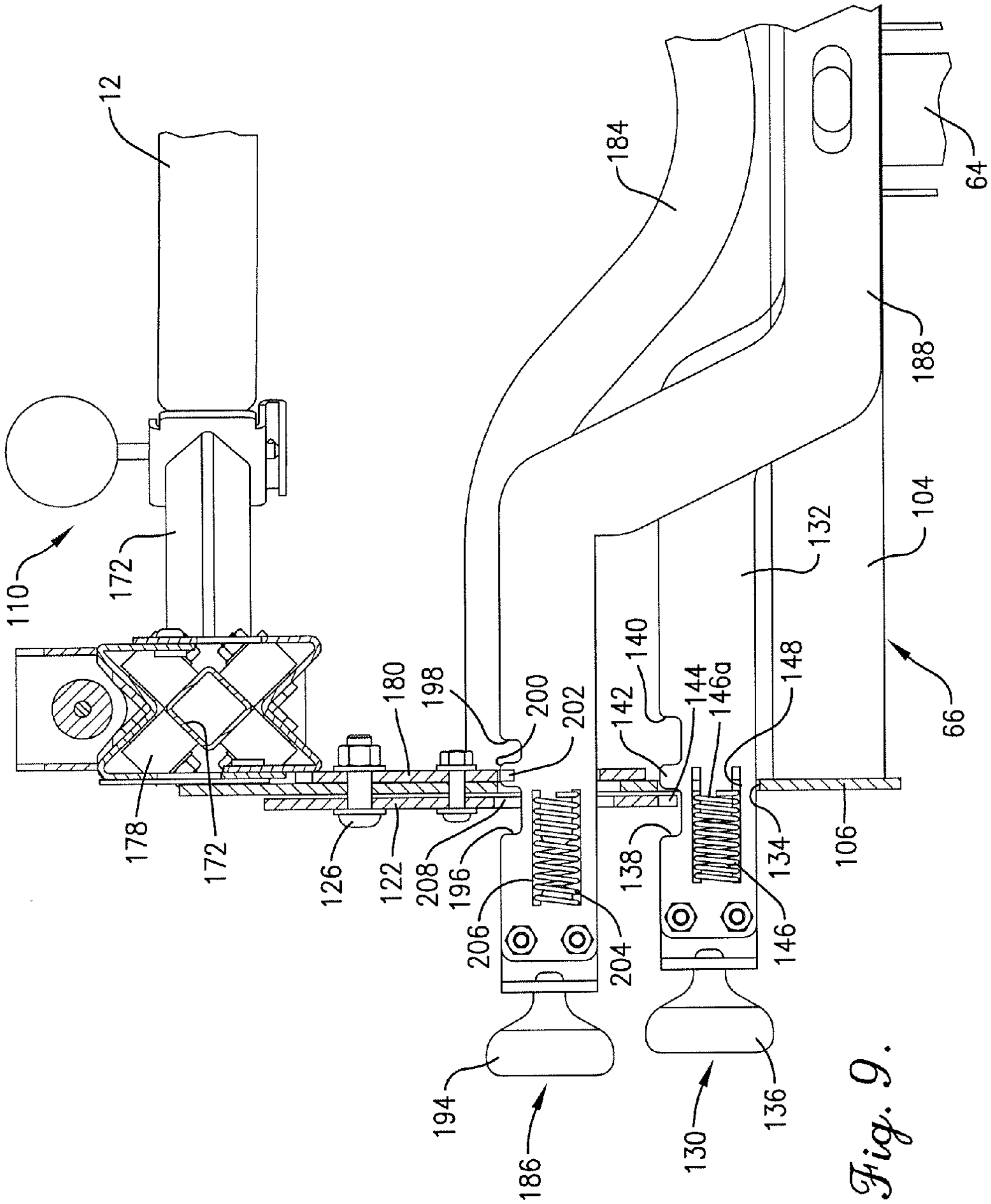
FIG. 9 is an enlarged, fragmentary vertical cross sectional view through the left upper portion of the machine taken substantially along line 9-9 of FIG. 5.
Figure 10:
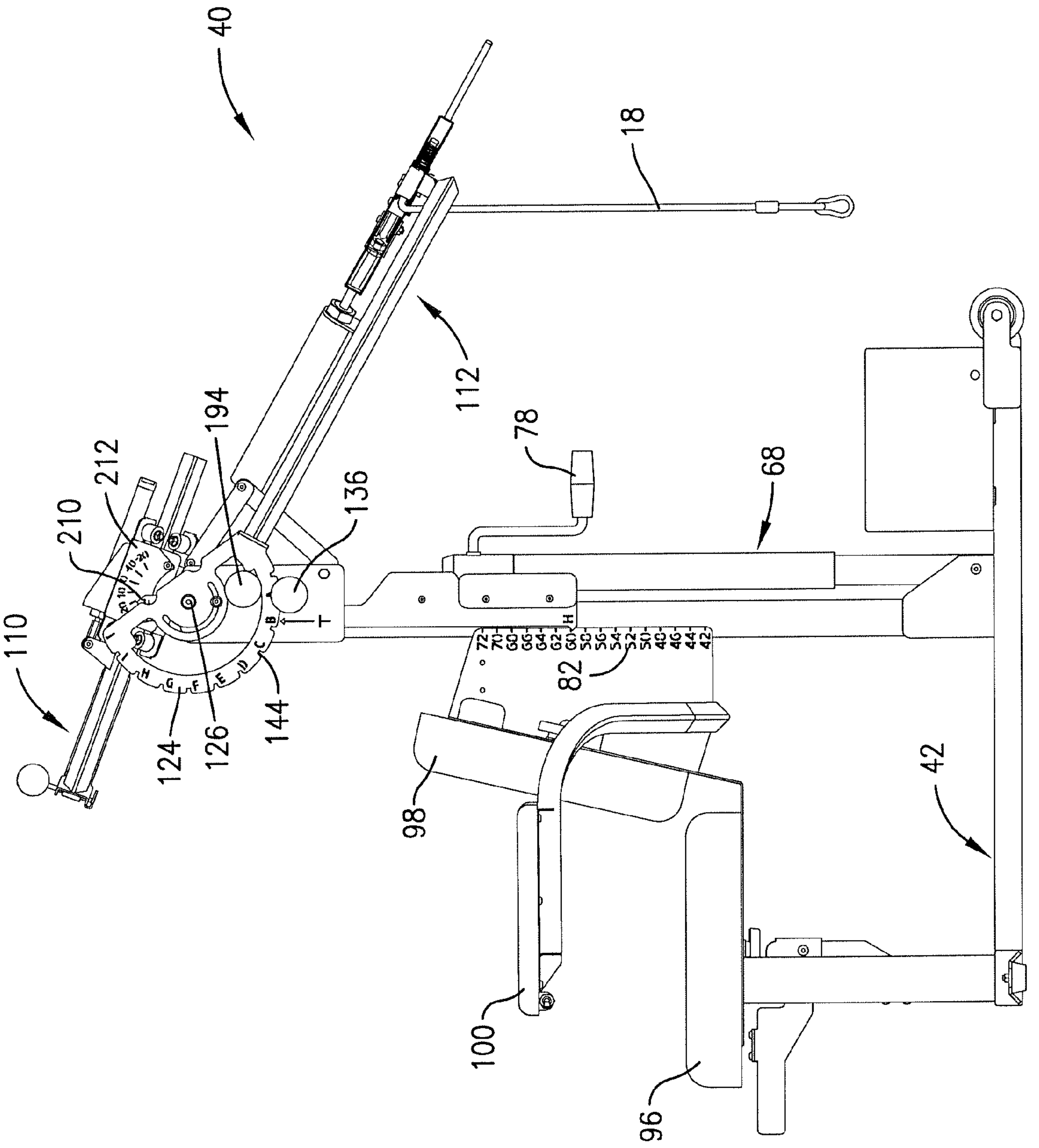
FIG. 10 is a left side elevational view of the machine illustrating the way in which the operating height and angle of force application of the fulcrum assembly and traction assembly can be adjusted.

Knobs 194 on opposite ends of lock bar 188 facilitate longitudinal shifting thereof between latched and unlatched positions. In this respect, a pair of notches 196 and 198 adjacent each end of lock bar 188 and along the upper edge thereof are separated by an upright locking tab 200. Depending upon the longitudinal shifted or unshifted position of lock bar 188, either tab 200 or one or the other of notches 196 and 198 will be in alignment with one of a series of notches 202 in the upper edge of clearance opening 192 in the corresponding mounting plate 180 or 182 (FIG. 4). In the latched position of FIG. 9, the tab 200 is aligned with a selected notch 202 such as to retain the fulcrum assembly 110 in a selected position of angular adjustment about pivots 126, 128. However, when lock bar 188 is shifted inwardly or outwardly relative to the latched position of FIG. 9, one or the other of the notches 196, 198 will come into alignment with the corresponding mounting plate 180, 182 so as to unlatch fulcrum assembly 110 and permit pivotal adjustment about pivots 126, 128. A compression spring 204 at each end of lock bar 188 is captured within an aperture 206 and bears against the outer surface of the corresponding end plate 106, 108 so as to center lock bar 188 in the neutral or latched position of FIG. 9.

It will be noted that each of the crescents 122, 124 has an arcuate cutout 208. Such cutout 208 allows lock bar 188 to project outwardly through crescents 122, 124 at its opposite ends without interference. As an aid to the doctor in determining the proper angle of adjustment for fulcrum assembly 110, each of the end plates 106, 108 is provided with an upwardly directed pointer 210. Each pointer 210 overlies a corresponding indicator plate 212 that is fixed to the upper extremity of the corresponding mounting plate 180 or 182. Numerical indicia or other markings on each indicator plate 212 are pointed to by the pointer 210.

Fulcrum assembly 110 further includes a pair of fluid-pressure-operated power devices 214 and 216 above the two roller guides 176, 178 and fixedly attached to bracketry associated with such guides. In a most preferred embodiment, the power devices 214 and 216 comprise air cylinders operated by a source of pressurized air, preferably the same source as utilized for traction air cylinder 150. It will be apparent that other types of power devices could be utilized in lieu of all of the air cylinders including, without limitation, hydraulic cylinders, electrical motors, and hydraulic, air, and electric actuators.

Each fulcrum assembly arm 172, 174 has an upstanding lug 218 to which the rod 220 of the corresponding air cylinder 214 or 216 is attached. As rods 220 of air cylinders 214, 216 are extended by pressurized air or inert gas, the fulcrum arms 172, 174 are pushed forwardly to apply fulcrum force via fulcrum member 12 against the posterior portion of the patient's cervical spine region. The amount of air pressure within fulcrum cylinders 214, 216 and the rate of increase or decrease thereof is controlled by control mechanism hereinafter more fully described.

It is desirable to keep the fulcrum arms 172, 174 moving in unison within their roller guides 176, 178. To accomplish this objective, linkage mechanism broadly denoted by the numeral 222 interconnects the rear ends of arms 172, 174. Mechanism 222 comprises a first elbow linkage 224 connected with left arm 172, a second elbow linkage 226 connected to arm 174, and a rock shaft 228 spanning the two linkages 224, 226 and fixedly secured thereto adjacent the lower ends thereof. Opposite ends of rock shaft 228 are journaled in lower portions of the corresponding end plates 106 and 108 of cross head 66.

Figure 15:
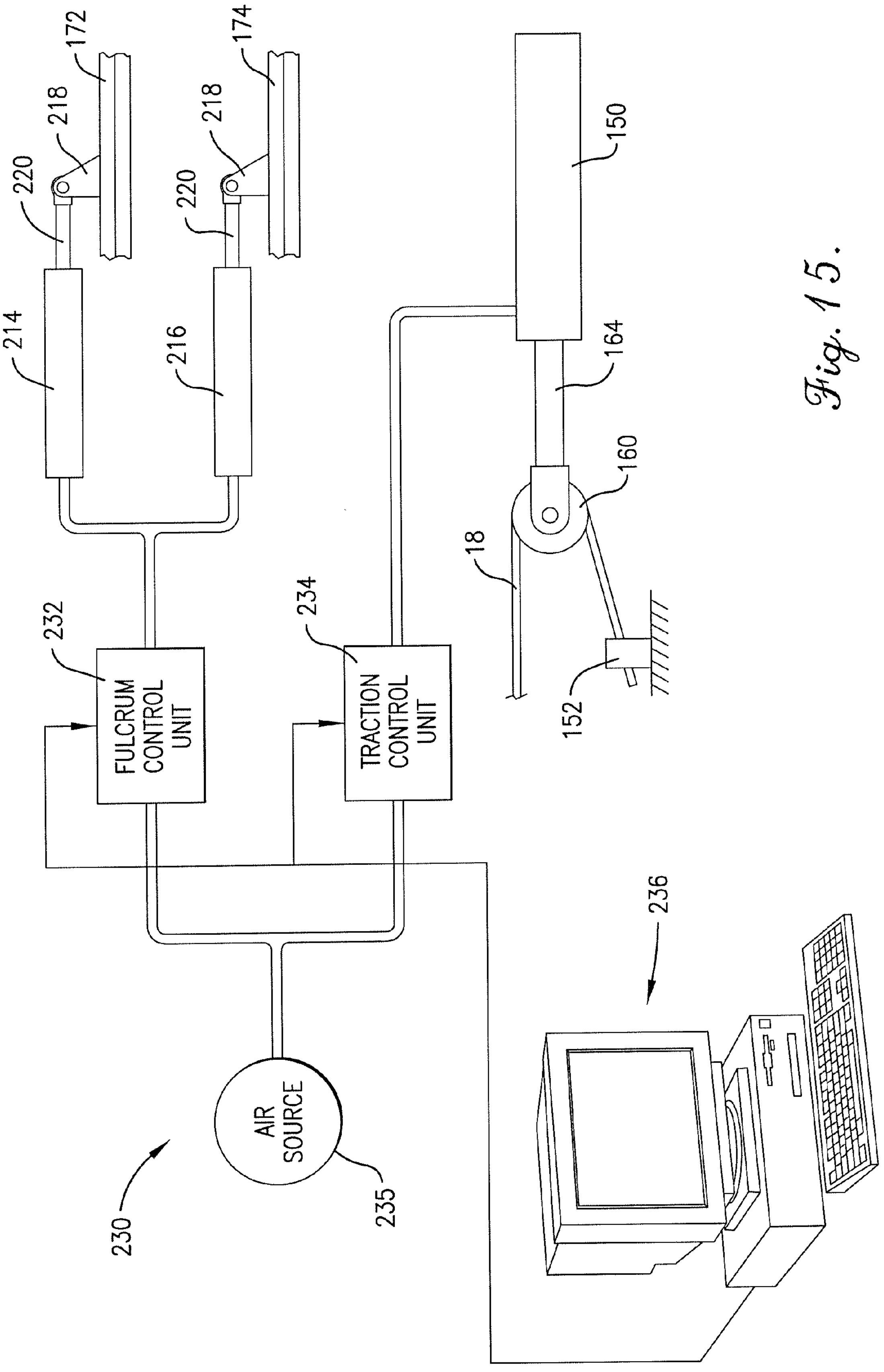
FIG. 15 is a schematic illustration of a control system for the fulcrum assembly and traction assembly of the machine.

FIG. 15 shows one embodiment of a control system 230 for controlling application of the fulcrum force F and traction force T during a treatment period. In the illustrated embodiment, control system 230 includes a pair of electro-pneumatic control units 232 and 234 that are interposed in the supply lines between a source of pressurized gas 235 and the air cylinders of the fulcrum assembly and traction assembly. Control units 232 and 234 may be housed within a box 237 on the rear of base 44 and are networked to a suitable controller such as a programmable logic controller or, in the illustrated embodiment, a computer 236. Computer 236, in turn, is programmed in such a manner as to provide electrical control signals to control units 232 and 234 for regulating the admittance of pressurized air to fulcrum cylinders 214, 216 and traction cylinder 150. While computer 236 can control a number of machines simultaneously, only a single machine has been illustrated in FIG. 15.

One suitable control unit for carrying out the functions of control units 232, 234 is a Marsh Bellofram 3000 series digital pressure controller available from Marsh Bellofram Corporation of Newell, W. Va. These control units utilize pulse-width modulated solenoid valves, an onboard pressure sensor, and digital signal processing, along with feed-and-bleed technology. An internal supply solenoid valve feeds supply pressure to the corresponding fulcrum or traction air cylinders. The internal exhaust solenoid valve bleeds off over pressure. By monitoring the onboard pressure sensor, the solenoids are rapidly fired to maintain or achieve a desired set point. The output of control units 232, 234 is directly related to the value of the electrical signal inputted to units 232, 234 under the control of computer 236.

Figure 1:
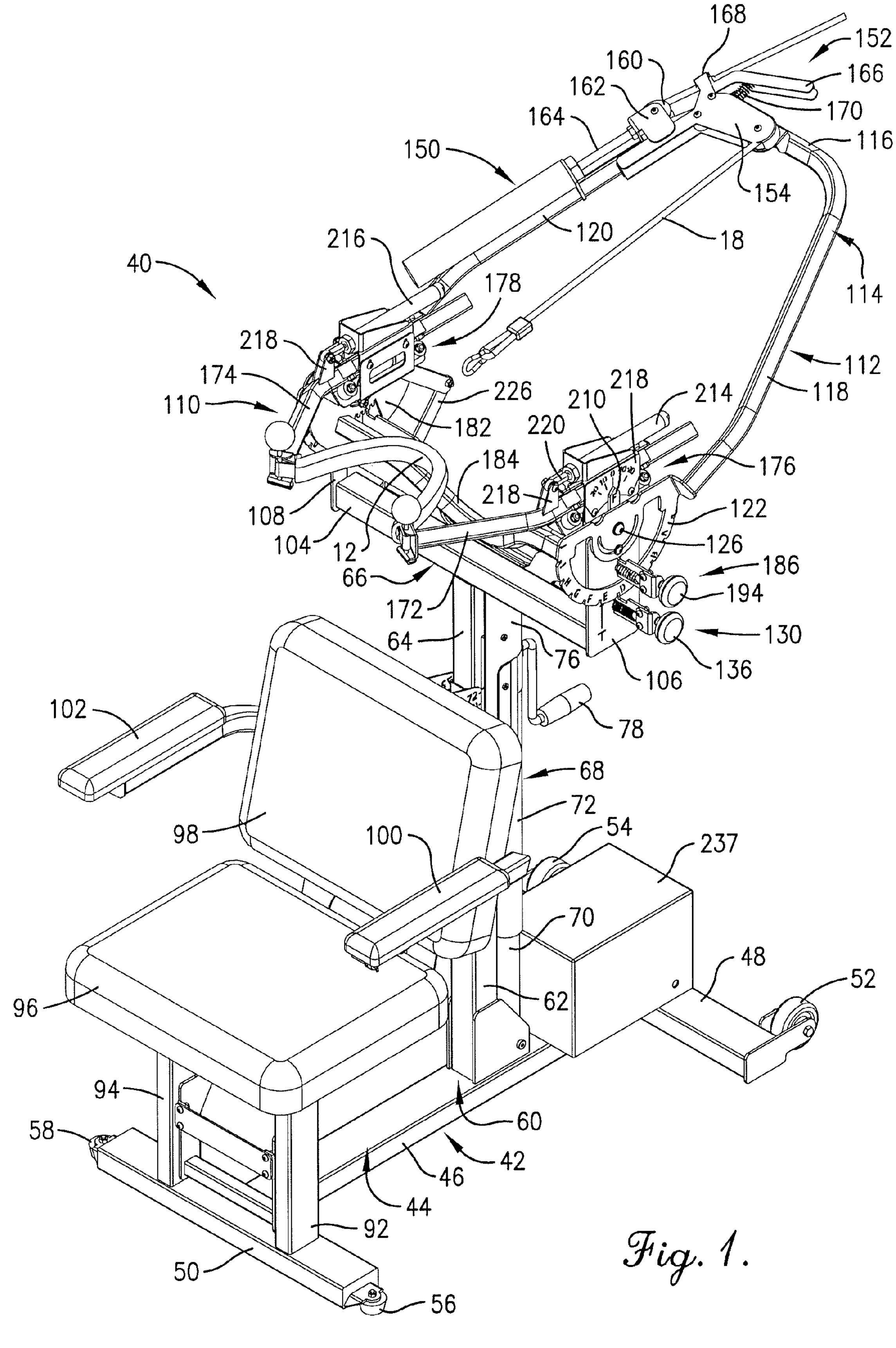
FIG. 1 is a left front perspective view of one embodiment of a machine constructed in accordance with the principles of the present invention and capable of carrying out our novel methods.
Figure 2:
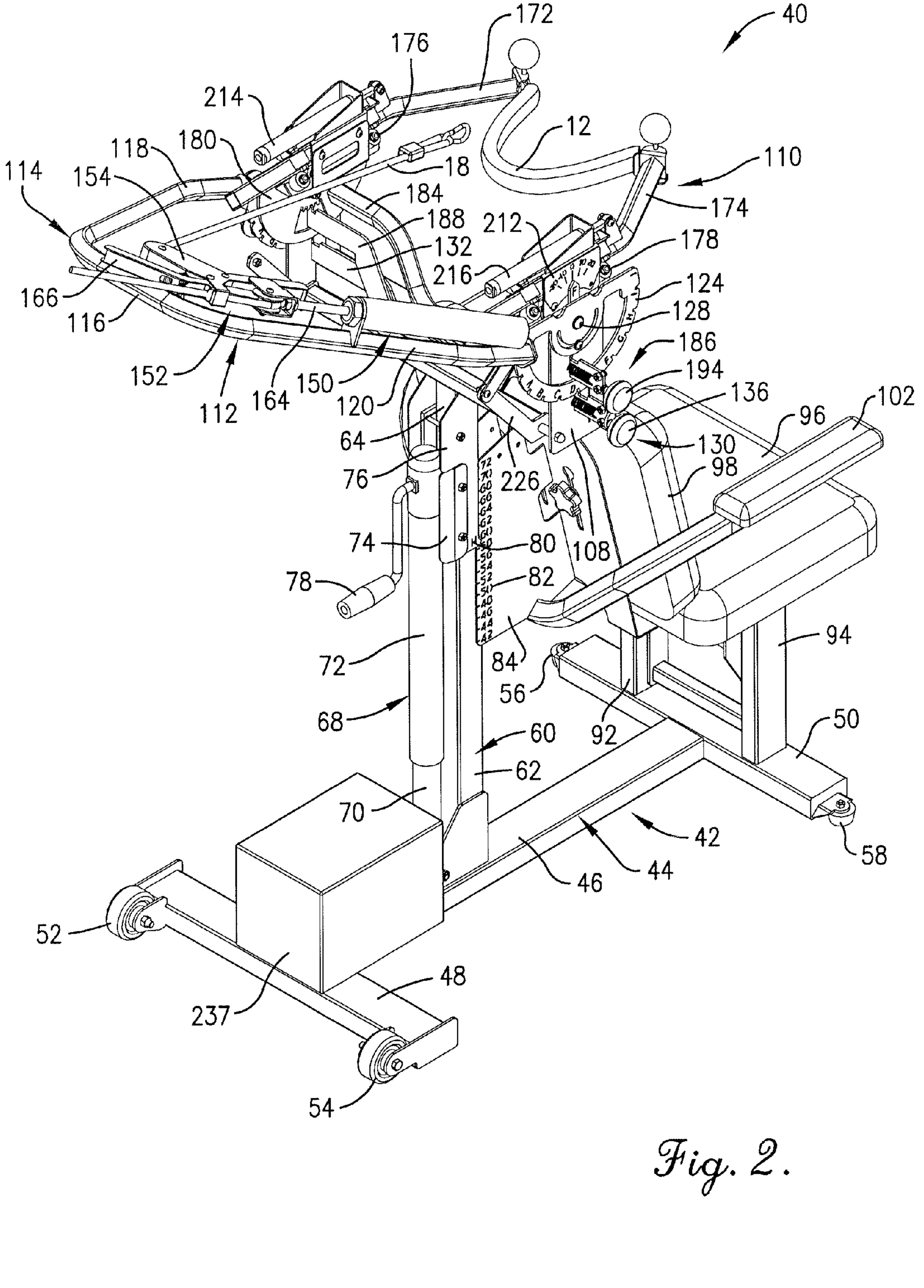
FIG. 2 is a right, rear perspective view thereof.
Figure 3:
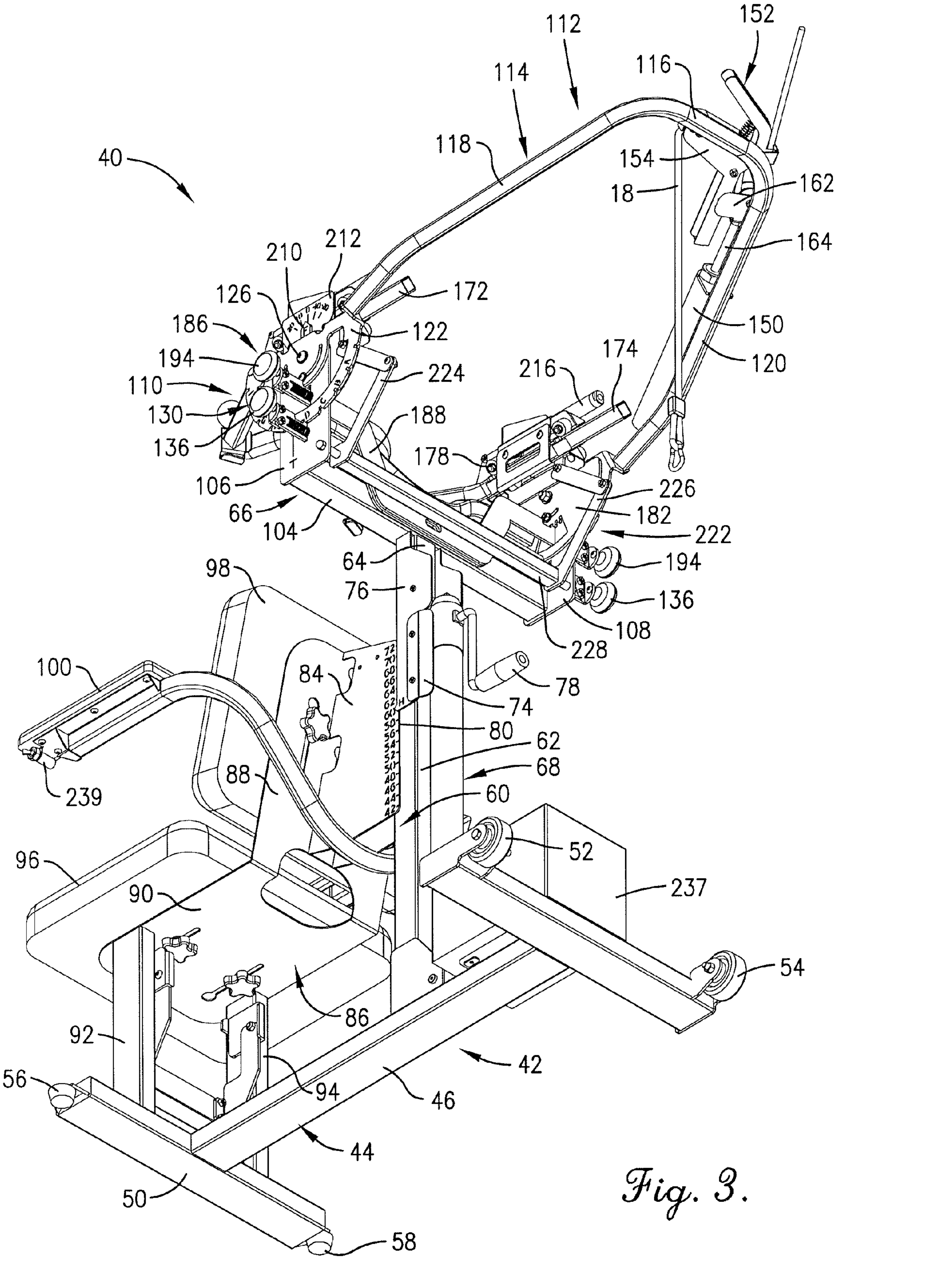
FIG. 3 is a left, rear perspective view of the machine from below the machine.

It is to be understood that control system 230 also includes one or more safety switches by which cylinders 150, 214, and 216 can be instantly exhausted to depressurize the fulcrum and traction assemblies. One of such switches (switch 239 in FIG. 3) may be advantageously located on one of the arm rests 100, 102 to permit the patient to immediately override the computer236 and stop the treatment if the need arises.

Figure 11A:
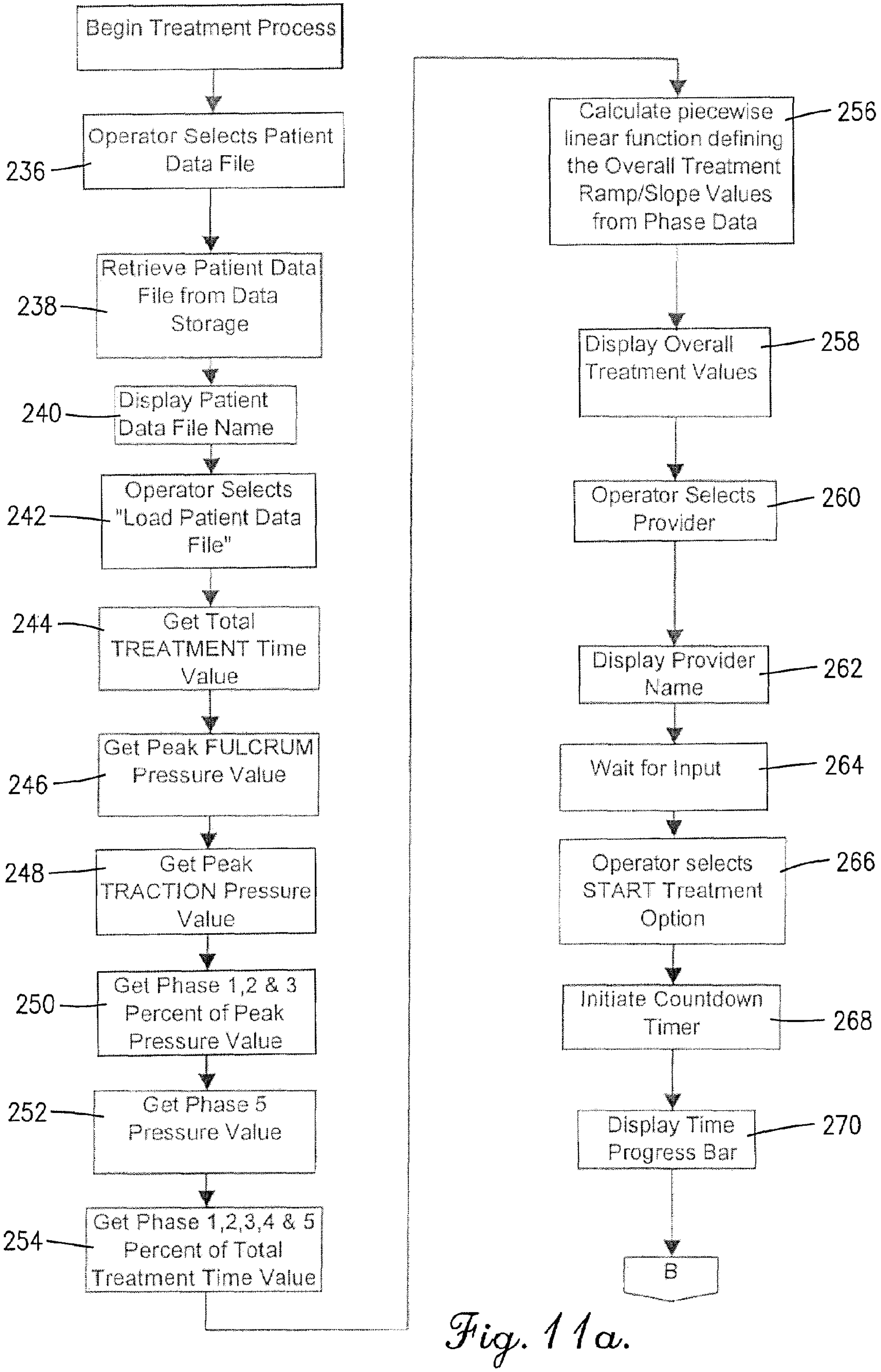
FIGS. 11*a* and 11*b* comprise a flow diagram broadly depicting the functionality and operation of a preferred implementation of a computer program according to the present invention.
Figure 11B:
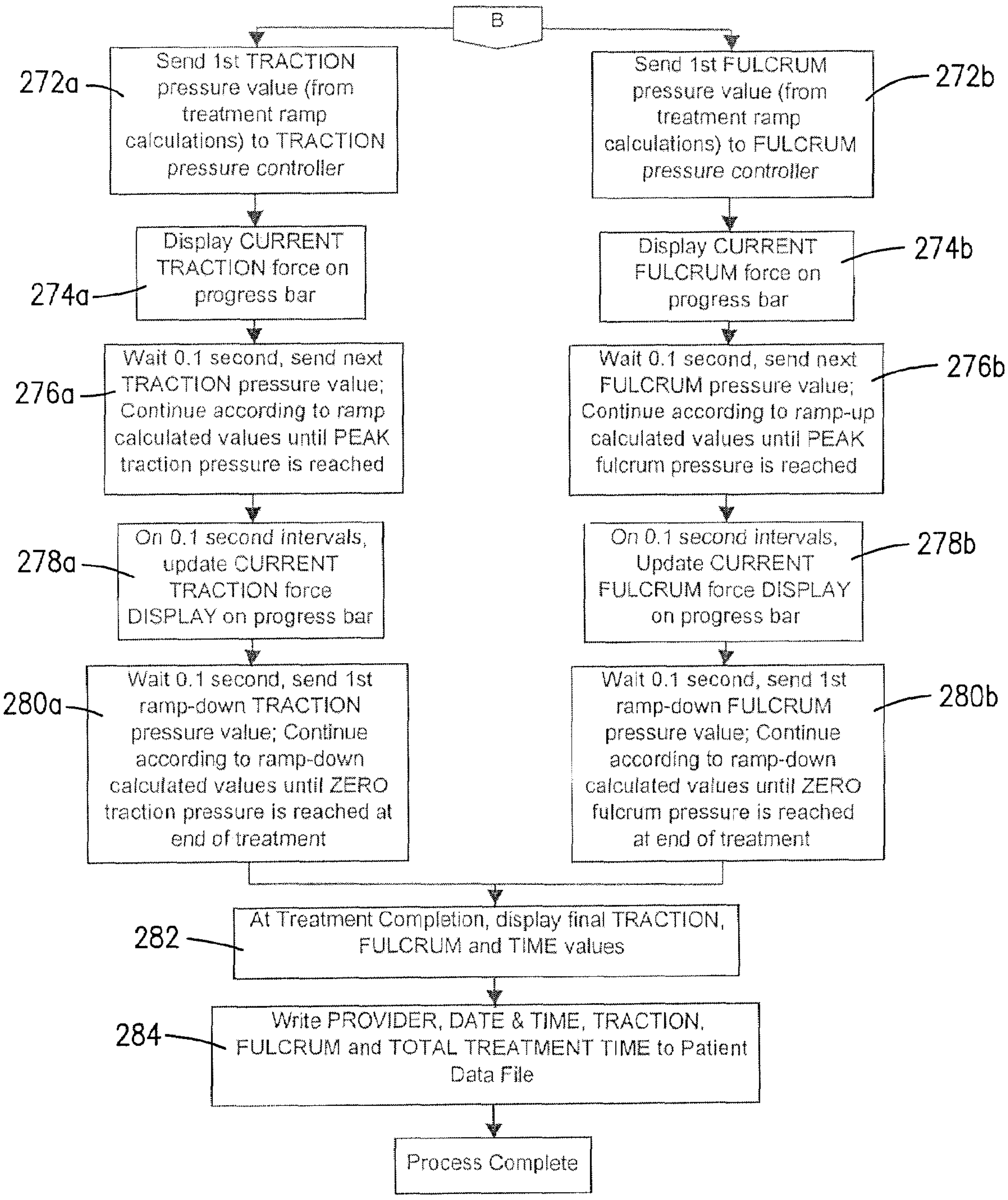

FIGS. 11*a* and 11*b* show steps carried out in accordance with the present invention. To begin the treatment process the operator selects the appropriate patient data file at step 236. Such a file is illustrated in FIG. 13 and previously described. At steps 238, 240 and 242 the operator causes the patient data file to be retrieved from data storage, displayed, and loaded. At step 244 the total treatment time value is obtained for that particular session or treatment, such as five minutes for treatment number 1 in column 22 of the chart of FIG. 13. At step 246, the peak fulcrum pressure value is obtained for that particular treatment number, such as fifteen pounds as appearing in column 24 for treatment number one in FIG. 13. Next, the peak traction pressure value is obtained at step 248, such as eighteen pounds in column 26 for treatment number 1 in FIG. 13.

At step 250, the phase 1, 2 and 3 percentages of peak pressure values are obtained, corresponding to the values in columns 30 of those phases for treatment number 1 in FIG. 13. The peak value for phase 4 has already been obtained at steps 246 and 248, since the peak value reached at the end of phase 4 is the peak value for the entire treatment period. At step 252 the percentage of peak pressure value for phase 5 is obtained, which should at the beginning correspond to the peak value at the end of phase 4 and be zero at the end of phase 5. At step 254, the various percentages of total treatment time values are obtained from columns 28 for phases 1, 2, 3, 4 and 5 for the appropriate treatment which, in this example, is treatment number 1.

Step 256 calculates the rate of increase in the fulcrum force F and the traction force T over predetermined periods of time during the treatment period. As noted earlier, in a most preferred embodiment, both the fulcrum force F and the traction force T increase continuously and smoothly during at least a significant portion of the treatment period, preferably throughout the first four time phases as illustrated in FIG. 14, until declining rapidly in the fifth time phase. The calculation for the rate of increase of the fulcrum force F and traction force T is sometimes referred to as a "piecewise linear function." In this calculation, and with respect to both the fulcrum and traction forces, the overall rate of force increase for both the preceding and following time phases are calculated to arrive at a smooth, yet progressive and continuous rate of advance. The percentages of peak force at the end of each of the respective time phases may be referred to as the "benchmark" force, and the system carries out its calculations in such a manner that the respective benchmark force values are achieved exactly at the end of the respective time phases.

At step 258, the overall treatment values are displayed on screen 32 as illustrated in FIG. 12, and at steps 260 and 262 the operator selects the name of the practitioner providing the treatment and causes such name to be displayed. Thereupon, the system waits at step 264 for the operator to initiate the treatment at step 266 by clicking on the "start" button in the window 32 of FIG. 12. At the initiation of the treatment period, a countdown timer within the program commences at step 268, and the progress of the treatment is displayed at step 270.

At companion steps 272*a* and 272*b* the calculated pressure values for traction pressure and fulcrum pressure are implemented in electrical signals to control units 232 and 234 to operate air cylinders 150, 214 and 216 accordingly. At steps 274*a* and 274*b* the current level of traction and fulcrum forces are displayed on screen 32. At steps 276*a* and 276*b* the system waits for a certain amount of time, depending upon the degree of continuity that has been programmed for the pressure increase. In a most preferred embodiment, it has been found that a wait of 0.10 seconds provides quite smooth and comfortable increases, but longer or shorter waits are certainly possible. Even a wait of one minute or more may sometimes be acceptable, although not ideal because it will make the force increases more noticeable to the patient. Waits of less than ten seconds each will generally make the force increases seem substantially continuous.

In the illustrated embodiment at steps 274*a* and 274*b* the system waits for 0.10 seconds and then sends the next calculated pressure values in the form of corresponding electrical signals to control units 232 and 234. This cycle continues at increments of 0.10 seconds until the peak traction and fulcrum pressures are reached, such ongoing values being continuously displayed on the progress bars of screen 32 in FIG. 12 at steps 278*a* and 278*b*. Thereafter, the system waits 0.10 seconds at steps 280*a* and 280*b* for the first calculated values for traction force and fulcrum force decrease to be signaled electrically to control units 232 and 234. Then, the decreasing cycle continues rapidly using the calculated values until zero traction pressure and zero fulcrum pressure are reached at the end of phase 5.

At the end of the treatment the final traction, fulcrum, and time values are displayed at step 282, and the various provider, date, and time information is written to the patient data file at step 284. This completes the process.

It will be seen that the present invention provides the doctor with a high degree of flexibility in creating a treatment plan that is customized for each individual patient, taking into account the numerous physiological and other factors established through initial examination of the patient. With the present invention, the doctor can easily establish and implement traction values for each individual patient that are just high enough to gently stretch the patient's soft tissues without being excessive throughout the treatment period. This results in more comfort and sense of security for the patient and increases the likelihood that the patient will complete the total number of treatments determined by the doctor to be necessary to achieve the best results.

As the present invention is used to implement the doctor's prescribed treatment plan, it allows the traction forces to be increased in a manner that takes advantage of the predicted yield rate (accommodation) of the patient's soft tissues surrounding the spine. The traction forces increase throughout most of the treatment period and are arranged to closely match the anticipated yield rate of the soft tissues. The more frequently these increases occur during the treatment, the greater the comfort level experienced by the patient. This increased comfort level allows the patient to tolerate more aggressive peak forces and results in increased biomechanical structural change of the spine. In a most preferred embodiment, a frequency of approximately ten times per second is utilized. However, other frequencies that are orders of magnitude higher or lower than this may be used. A frequency as low as four pressure increases per entire treatment period could still provide improved patient comfort and increased effectiveness compared to conventional traction methods.

It should also be apparent that the preferred apparatus for carrying out the principles of our invention is designed in such a way that all applied forces occur outside the visual field of the patient, i.e., behind him. Note in this respect that the fulcrum cylinders 214, 216 in essence push on the fulcrum member 12 from behind the patient's head rather than pull on the member from in front of his head. This helps avoid any feelings of claustrophobia on the part of the patient while he is being treated.

The automatic nature of the machine and treatment implemented thereby enables the doctor to start the treatment and carry it through to completion without his further intervention. This frees the doctor to attend to other matters while the treatment is carried out, and allows the patient to remove himself from the machine without assistance when the treatment is completed.

The compact size of the machine allows efficient layout of the doctor's office and is less intimidating to patients than conventional equipment. It also permits the doctor to have a number of machines placed within the office and in operation at any one time, all of which can be effectively monitored and controlled using a single computer.

Those skilled in the art will appreciate that in some instances it may be desirable to utilize a back rest, particularly the top edge thereof, as a fulcrum member. In other instances there may be no fulcrum member at all. Thus, it is to be understood that the term "fulcrum member" as used herein is not necessarily limited to a separate and distinct component such as the strap-like fulcrum member 12 hereinabove described.

It will also be appreciated that many of the principles of the present invention need not be limited to a method and apparatus for treating the cervical region of the spine. For example, they may also be utilized in treating the lumbar and/or thoracic regions of a patient's spine. The use of progressively increasing, laterally and oppositely directed forces can be especially beneficial.

The inventor(s) hereby state(s) his/their intent to rely on the Doctrine of Equivalents to determine and assess the reasonably fair scope of his/their invention as pertains to any apparatus not materially departing from but outside the literal scope of the invention as set out in the following claims.

The invention claimed is:

1. Apparatus for bending a person's spine to change the shape thereof, said apparatus comprising:

a traction assembly for applying a traction force to the spine at an angle to the longitudinal axis of the spine to bend the spine; and control mechanism for controlling said traction force in such a manner that the percentage of peak value of the traction force is progressively increased over a predetermined period of time during the treatment period to gradually stretch tissues of the spine, said traction assembly including a headgear adapted to be worn by the person being treated and a fluid-pressure-operated power device operably connected with the headgear, said control mechanism including a control unit operably connected with said power device and adapted for connection with a source of pressurized fluid for supplying progressively increasing levels of pressurized fluid to the device in response to receiving electrical control signals.

2. Apparatus as claimed in claim 1, said fluid-pressure-operated power device being pneumatically operated.

3. Apparatus for bending a person's spine to change the shape thereof, said apparatus comprising:

a traction assembly for applying a traction force to the spine at an angle to the longitudinal axis of the spine to bend the spine; and control mechanism for controlling said traction force in such a manner that the percentage of peak value of the traction force is progressively increased over a predetermined period of time during the treatment period to gradually stretch tissues of the spine, said control mechanism being operable to increase the traction force substantially continuously over the predetermined period.

4. Apparatus for bending a person's spine to change the shape thereof, said apparatus comprising:

a traction assembly for applying a traction force to the spine at an angle to the longitudinal axis of the spine to bend the spine; and control mechanism for controlling said traction force in such a manner that the percentage of peak value of the traction force is progressively increased over a predetermined period of time during the treatment period to gradually stretch tissues of the spine, further comprising a fulcrum member disposed for application against the spine, said traction assembly being operable to bend the spine about the fulcrum member while exerting the traction force.

5. Apparatus as claimed in claim 4, said control mechanism being operable to apply a fulcrum force with said fulcrum member and to progressively increase the percentage of peak value of the fulcrum force over a predetermined period of time during the treatment period.

6. Apparatus as claimed in claim 5, said fulcrum member comprising part of a fulcrum assembly that includes a fluid-pressure-operated power device operably connected with said fulcrum member, said control mechanism including a control unit operably connected with said power device and adapted for connection with a source of pressurized fluid for supplying progressively increasing levels of pressurized fluid to the device in response to receiving electrical control signals.

7. Apparatus as claimed in claim 6, said fluid-pressure-operated power device being pneumatically operated.

8. Apparatus as claimed in claim 5, said control mechanism being operable to increase the percentage of peak value of the fulcrum force substantially continuously over the predetermined period.

9. Apparatus as claimed in claim 5, said traction assembly including a headgear adapted to be worn by the person being treated and a fluid-pressure-operated power device operably connected with said headgear, said control mechanism including a traction control unit operably connected with said power device and adapted for connection with a source of pressurized fluid for supplying substantially continuously increasing levels of pressurized fluid to the device in response to receiving electrical control signals.

10. Apparatus as claimed in claim 5, said fulcrum assembly being so disposed that most of the fulcrum assembly is located behind the line of sight of the person being treated.

11. Apparatus for bending a person's spine to change the shape thereof, said apparatus comprising:

a traction assembly for applying a traction force to the spine at an angle to the longitudinal axis of the spine to bend the spine; and control mechanism for controlling said traction force in such a manner that the percentage of peak value of the traction force is progressively increased over a predetermined period of time during the treatment period to gradually stretch tissues of the spine, said traction assembly being mounted on a frame, said frame having a seat and a backrest coupled with said frame for supporting the person being treated in a seated position.

12. Apparatus for bending a person's spine to change the shape thereof; said apparatus comprising:

a traction assembly for applying a traction force to the spine at an angle to the longitudinal axis of the spine to bend the spine; and control mechanism for controlling said traction force in such a manner that the percentage of peak value of the traction force is progressively increased over a predetermined period of time during the treatment period to gradually stretch tissues of the spine, further comprising a programmable controller coupled with said control mechanism.

13. Apparatus as claimed in claim 12, said programmable controller including a computer and a program installed on said computer.

14. Apparatus for bending the cervical region of a person's spine, said apparatus comprising:

a frame;

a seat and a back rest mounted on the frame for treating the person in a seated position;

a fulcrum assembly supported on said frame above the seat and including a fulcrum member disposed for applying a fulcrum force against the posterior portion of the cervical region during a treatment period, said fulcrum assembly including a fluid-pressure-operated power device operably coupled with said fulcrum member for applying said fulcrum force;

a traction assembly supported on said frame above the seat and including a headgear adapted to be worn by the person being treated for applying a traction force in a direction at an angle to the longitudinal axis of the spine to bend the cervical region about the fulcrum member, said traction assembly further including a second fluid-pressure-operated power device operably coupled with said headgear for applying said traction force; and control mechanism for supplying pressurized fluid to the power devices during the treatment period, said fulcrum assembly and said traction assembly being located primarily above and behind the back rest outside the visual field of the person when the person is in the seated position on the seat.

15. Apparatus as claimed in claim 14, said control mechanism being operable to progressively increase the percentage of peak value of the fulcrum force and the percentage of peak value of the traction force during a predetermined period of the treatment period.

16. Apparatus as claimed in claim 15, said control mechanism being operable to increase the percentage of peak value of the fulcrum force and the percentage of peak value of the traction force substantially continuously during said predetermined period.

17. Apparatus as claimed in claim 14, said fluid-pressure-operated power devices being operated by pneumatic pressure.

18. Apparatus as claimed in claim 14, said control mechanism including control units operably coupled with said power devices for supplying pressurized fluid thereto in response to electrical control signals during the treatment period.

19. Apparatus as claimed in claim 18, said control mechanism further including a controller programed to provide electrical control signals to the control units.

20. Apparatus as claimed in claim 14, said frame including a stationary lower portion and a vertically adjustable upper portion, said fulcrum assembly and said traction assembly being mounted on said upper portion to permit height adjustment of said assemblies to fit the person being treated.

21. Apparatus as claimed in claim 14, said traction assembly being angularly adjustable about a transverse horizontal axis relative to said frame and the fulcrum assembly for adjusting the angle of application of the traction force.

22. Apparatus as claimed in claim 14, said fulcrum assembly being angularly adjustable about a transverse horizontal axis relative to said frame and the traction assembly for adjusting the angle of application of the fulcrum force.

23. Apparatus as claimed in claim 14, said fulcrum member comprising a strap.

* * * * *